United States Patent [19]

Nakamura

[11] Patent Number: 4,830,823
[45] Date of Patent: May 16, 1989

[54] DENTAL TITANIUM ALLOY CASTINGS
[75] Inventor: Seizo Nakamura, Osaka, Japan
[73] Assignee: Ohara Co., Ltd., Osaka, Japan
[21] Appl. No.: 97,785
[22] Filed: Sep. 18, 1987
[30] Foreign Application Priority Data Jan. 28, 1987 [JP] Japan ................................. 62-19243

[51] Int. Cl.$^4$ .......................... H07L 7/85; C22C 14/00
[52] U.S. Cl. .................................................... 420/420
[58] Field of Search ........................ 420/420; 148/32.5
[56] References Cited

U.S. PATENT DOCUMENTS

| | | | |
|---|---|---|---|
| 2,819,958 | 1/1958 | Abkowitz et al. | 75/175.5 |
| 2,893,864 | 7/1959 | Harris et al. | 420/420 |
| 3,679,403 | 7/1972 | Bomberger, Jr. et al. | 420/420 |
| 4,040,129 | 8/1977 | Steinemann et al. | 420/420 |
| 4,197,643 | 4/1980 | Burstone et al. | 420/420 |

FOREIGN PATENT DOCUMENTS 0447450  10/1974  U.S.S.R. ............................. 420/420

OTHER PUBLICATIONS

Kessler in Titanium Science & Technology, ed. Jaffee et al., Plenum, N.Y. 1973, p. 303.

Primary Examiner—Upendra Roy
Attorney, Agent, or Firm—Armstrong, Nikaido Marmelstein Kubovcik & Murray

[57] ABSTRACT

Dental titanium alloy castings have physical properties equal to physical characteristics incidental to a Ti-6Al-4 V alloy can be obtained by casting titanium alloys containing aluminium at a ratio of 1.5 to 4.0% by weight and vanadium at a ratio of 1.0 to 3.0% by weight.

2 Claims, No Drawings

DENTAL TITANIUM ALLOY CASTINGS

BACKGROUND OF THE INVENTION

1. Field of the Invention

The present invention relates to dental titanium castings, in particular to dental castings produced by casting titanium alloys containing a specified quantity of vanadium and aluminium.

2. Description of the Prior Art

Titanium and its alloys have superior physical characteristics, such as lightweightness and increased mechanical strength, and superior chemical corrosion resistance, so that they have been recently used in flying machines, space rockets, chemical plants and the like frequently, and they have a superior wetting property, so that they have been frequently used as a living body material such as dental making-up substance. In particular, Ti-6Al-4V alloy (titanium alloy containing aluminium at a ratio of 6% by weight and vanadium at a ratio of 4% by weight) is well known as a titanium alloy for used in flying machines. This alloy has physical characteristics superior to those of pure titanium, as shown in Table 1.

TABLE 1

|  | pure titanium | Ti—6 Al—4 V |
| --- | --- | --- |
| Tensile strength (Kgf/mm$^2$) | 35–50 | 91–95 |
| Elongation (%) | 23 | 15 |
| Hardness (Hv) | 110–150 | 300 |

Accordingly, taking notice of superior physical characteristics of this Ti-6Al-4V alloy, it has been published in many papers that it is used as a living body material. Also in the dentistry, it has been intended to use this alloy for dental making-up substances such as inplants and metallic beds.

However, in the above described cases of flying machines and the like, since the parts are generally large-sized, they can be produced by a method other than the casting, such as the forging, but in the cases of small-sized and complicated in shape parts, such as dental making-up substances, they are difficult to produce by methods other than the casting. However, in the case where a Ti-6Al-4V alloy is cast, castings merely subjected to the casting cannot reproduce physical characteristics of the original alloy. That is to say, they are hard and brittle. Accordingly, in order to use them in dentistry, a remarkably troublesome after-treatment, such as a heat treatment under a high vacuum atmosphere after the casting, is required, whereby they have never been practically used as dental castings.

SUMMARY OF THE INVENTION

The present invention was achieved on the basis of knowledge that castings having superior physical characteristics as dental titanium alloy castings can be obtained by casting a titanium alloy containing a specified quantity of aluminium and vanadium given by the repeated earnest investigations aiming at the solution of the above described problem. That is to say, it is an object of the present invention to provide dental titanium alloy castings, which can be used in dentistry as they are, having physical characteristics equal to those of a Ti-6Al-4V alloy and more superior than those of pure titanium, and meeting various kinds of physical property, such as tensile strength, elongation and hardness, requied for dental castings, by casting a titanium alloy containing aluminium (Al) at a ratio of 1.5 to 4.0%, preferably 3.0%, by weight and vanadium at a ratio of 1.0 to 3.0%, preferably 2.5%, by weight.

DETAILED DESCRIPTION OF THE INVENTION

Dental titanium alloy castings according to the present invention will be below described in more detail.

In order to produce dental titanium alloy castings according to the present invention, general methods of casting titanium or titanium alloys may be used. For example, the argon arc fusion, high-frequency fusion and the like can be suitably adopted as a method of melting alloys to be cast. In addition, a casting method, such as centrifugal casting and suction-pressure casting, can be adopted.

Ceramic crucibles made of magnesium oxide, calcium oxide, zirconium oxide, yttria or the like singly or in combination, a crucible made of copper and the like can be adopted as a crucible for melting alloys.

Mold materials mainly comprising magnesium oxide, zirconium oxide and the like, those made of silica, alumina, mullite, spinel and the like singly or in combination, those prepared by further adding phosphate series binders and the like can be adopted.

Also a temperature condition and the like in the casting are not specially limited. The casting may be carried out at a temperature of the mold materials of normal temperature to about 400° C.

In order to obtain castings having physical characteristics superior to those of pure titanium castings after the casting and capable of being used as dental making-up substances, it is preferable to casta titanium alloy containing aluminium at a ratio of 1.5 to 4.0% by weight and vanadium at a ratio of 1.0 to 3.0% by weight. In particular, the castings obtained by casting a "Ti-3Al-2.5V alloy" containing aluminium at a ratio of 3.0% by weight and vanadium at a ratio of 2.5% by weight exhibit physical characteristics equal to those incidental to the Ti-6Al-4V alloy and more superior than those of pure titanium castings are preferable as dental titanium alloy castings.

In the case where the Ti-6Al-4V alloy itself is cast, superior characteristics incidental to said alloy are lost and as a result, it becomes hard and brittle, whereby it cannot be used in the dentistry under the condition merely cast. Also in the case where a titanium alloy containing merely aluminium or a titanium alloy containing merelyvanadium is cast, the resulting castings are brittle and cannot be used in the dentistry.

EXAMPLES

Various kinds of titanium alloy containing aluminium and vanadium were cast and the resulting castings were measured on physical property. The measured physical properties of the resulting castings were compared with those of pure titanium castings to investigate whether they can be used as dental castings or not.

In addition, in the casting a magnesia crucible was used as a crucible for melting an alloy, phosphate series mold materials mainly comprising silica and alumina being used, an argon arc type centrifugal casting machine (TITANIUMER: OHARA CO., LTD., OSAKA, JAPAN) being used, and the casting being carried out under the usual casting conditions.

In addition, the evaluation of the castings was carried out on the basis of the comparison with pure titanium and the castings of dental making-up substances and the like having a tensile strength of 70 kgf/mm² or more, an elongation of 10% or more and a hardness of about 200 to 350 were deemed as preferable ones.

by methods other than the casting, a titanium alloy containing aluminium at a ratio of 1.5 to 4.0% by weight and vanadium at a ratio of 1.0 to 3.0% by weight is cast to produce dental castings, such as implant castings,

TABLE 2

| Experiment | 1 | 2 | 3 | 4 | 5 |
|---|---|---|---|---|---|
| Alloy | Pure titanium (Ti) | Ti—6 Al—4 V | Ti—5 Al—3 V | Ti—4 Al—3 V | Ti—3 Al—2.5 V |
| Before the casting | | | | | |
| Tensile strength (kgf/mm²) | 35–50 | 91–95 | — | — | 70 |
| Elongation (%) | 23 | 15 | — | — | 24 |
| Hardness (Hv) | 110–150 | 300 | — | — | 130–150 |
| After the casting | | | | | |
| Tensile strength (kgf/mm²) | 65–75 | 70–75 | 70–75 | 70–80 | 80–90 |
| Elongation (%) | 15–20 | 5–8 | 5–8 | 10–12 | 10–15 |
| Hardness (Hv) | 190–240 | 350–360 | 350–360 | 320–350 | 300–330 |
| Evaluation | | x | x | | |

| Experiment | 6 | 7 | 8 | 9 | 10 |
|---|---|---|---|---|---|
| Alloy | Ti—2 Al—1.3 V | Ti—1.5 Al—1.0 V | Ti—1 Al—0.5 V | Ti—3 Al | Ti—2.5 V |
| Before the casting | | | | | |
| Tensile strength (kgf/mm²) | — | — | — | — | — |
| Elongation (%) | — | — | — | — | — |
| Hardness (Hv) | — | — | — | — | — |
| After the casting | | | | | |
| Tensile strength (kgf/mm²) | 70–80 | 70–80 | 55–65 | 40–50 | 40–50 |
| Elongation (%) | 10–15 | 10–12 | 10–12 | 4–6 | 8 |
| Hardness (Hv) | 280–320 | 260–280 | 190–240 | 300–350 | 280–330 |
| Evaluation | | | Δ | x | x |

*Tensile strength is measured in accordance with JIS-Z-2241.
*Elongation is measured in accordance with JIS-Z-2241.
*Hardness is measured by means of a Vickers hardness tester.

As obvious from Table 2, in the case where of various kinds of titanium alloy a Ti-6Al-4V alloy is cast (Experiment 2), the resulting castings are hard and brittle, whereby they cannot be used as dental castings as they are. Also in the case where a titanium alloy contains merely either aluminium or vanadium (Experiment 9 and 10), the resulting castings are brittle, whereby they cannot be used in the dentistry. Besides, although the castings of a titanium alloy containing aluminium at a ratio of 1.0% by weight and vanadium at a ratio of 0.5% by weight (Experiment 8) are usable, they do not exhibit any improvement of physical characteristics in comparison with those of pure titanium castings. Accordingly, they do not merit use. That is to say, the castings of titanium alloys containing aluminium at a ratio of 1.5 to 4% by weight and vanadium at a ratio of 1.0 to 3.0% by weight (Experiments 4 to 7) are superior to the castings of pure titanium in tensile strength and hardness, in particular the castings of a titanium alloy containing aluminium at a ratio of 3.0% by weight and vanadium at a raiio of 2.5% by weight, that is to say a Ti-3Al-2.5V alloy, (Experiment 5) have characteristics equal to those incidental to a Ti-6Al-4V alloy (not cast) but more superior to those of the castings of pure titanium, whereby being able to produce castings preferably usable as dental castings.

· As above described, as for small-sized and complicated in shape castings, which are difficult to produce metallic bed castings, metallic frame castings, crown bridge castings and artificial bones, whereby dental castings superior to the castings of pure titanium in physical characteristic and superior also in chemical corrosion resistance and wetting property can be obtained.

The present invention can be variously modified without departing from the spirit or main characteristics thereof. Accordingly, it should be understood that the above described preferred embodiment is merely an illustrative example in all respects. That is to say, it must not be restrictedly understood. The scope of the present invention is defined by what is claimed and not restricted by a text of the specification. Furthermore, the modifications and changes belonging to the equally divided scopes of what is claimed are all within what is claimed of the present invention.

What is claimed is:

1. A dental prosthesis produced by casting a titanium allow containing aluminium at a ratio of 1.5 to 4.0% by weight and vanadium at a ratio of 1.0 to 3.0% by weight.

2. A dental prosthesis as set forth in claim 1, in which a titanium alloy containing aluminium at a ratio of 3.0% by weight and vanadium at a ratio of 2.5% by weight is used as said titanium alloy.

* * * * *